United States Patent
Ahmed et al.

(10) Patent No.: US 8,609,568 B2
(45) Date of Patent: Dec. 17, 2013

(54) CATALYST FOR OXIDATIVE DEHYDROGENATION OF PROPANE TO PROPYLENE

(75) Inventors: Shakeel Ahmed, Dharhan (SA); Faizur Rahman, Dhahran (SA); Uwais Baduruthamal, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 453 days.

(21) Appl. No.: 12/897,686

(22) Filed: Oct. 4, 2010

(65) Prior Publication Data

US 2012/0083641 A1    Apr. 5, 2012

(51) Int. Cl.
*B01J 29/06*    (2006.01)
*B01J 21/06*    (2006.01)

(52) U.S. Cl.
USPC ............... 502/60; 502/63; 502/74; 502/240; 502/247; 502/259; 502/263

(58) Field of Classification Search
USPC ............... 502/60, 63, 74, 240, 247, 259, 263
See application file for complete search history.

(56) References Cited

U.S. PATENT DOCUMENTS

| | | | |
|---|---|---|---|
| 5,134,241 A | 7/1992 | Le et al. | |
| 6,239,325 B1 | 5/2001 | Kishimoto et al. | |
| 7,125,817 B2 | 10/2006 | Ou et al. | |
| 7,145,051 B2 | 12/2006 | Ou et al. | |
| 7,291,761 B2 * | 11/2007 | Machhammer et al. | 585/658 |
| 2002/0143198 A1 * | 10/2002 | Cheng et al. | 552/309 |
| 2004/0034266 A1 | 2/2004 | Brophy et al. | |
| 2005/0201920 A1 | 9/2005 | Shan et al. | |
| 2006/0052234 A1 | 3/2006 | Shan et al. | |
| 2008/0177117 A1 | 7/2008 | Benderly et al. | |
| 2009/0171109 A1 | 7/2009 | Benderly et al. | |
| 2009/0182186 A1 | 7/2009 | Benderly et al. | |
| 2009/0325790 A1 * | 12/2009 | Haller et al. | 502/241 |

FOREIGN PATENT DOCUMENTS

| | | |
|---|---|---|
| CN | 101219389 | 7/2008 |
| CN | 101380587 | 3/2009 |

OTHER PUBLICATIONS

Takehira et al., "CO2 Dehydrogenation of Propane over Cr-MCM-41 Catalyst", Studies in Surface Science and Catalysis, 153, 2004, pp. 323-328.*
Pena et al., "V-containing MCM-41 and MCM-48 catalysts for the selective oxidation of propane in gas phase", Applied Catalysis A: General 209, 2001, pp. 155-164.*
Lim et al., "Preparation of Highly Ordered Vanadium-Substituted MCM-41: Stability and Acidic Properties", J. Phys. Chem. B 106, 2002, Ps. 8437-8448.*
B. Solsona et al., "Vanadium Oxide Supported on Mesoporous MCM-41 as Seletive Catalysts in the Oxidative Dehydrogenation of Alkenes", Journal of Catalysis 203:443-452 (2001).
Rui Zhou et al., "Oxidative dehydrogenation of propane over mesoporous HMS silica supported vanadia", Catalysis Letters 75(1-2):107-112 (2001).
Yong-Mei Liu et al., "Vanadium oxide supported on mesoporous SBA-15 as highly selective catalysts in the oxidative dehydrogenation of propane", Journal of Catalysts 224:417-428 (2004).
Baba Y. Jibril and Shakeel Ahmed, "Oxidative dehydrogenation of propane over Co, Ni and Mo mixed oxides/MCM-41 catalysts: Effects of intra- and extra-framework locations of metals on product distributions", Catalysis Communications 7:990-996 (2006).

* cited by examiner

*Primary Examiner* — Elizabeth Wood
(74) *Attorney, Agent, or Firm* — Richard C. Litman

(57) ABSTRACT

The catalyst for oxidative dehydrogenation of propane to propylene includes vanadium and aluminum incorporated into the framework of a mesoporous support, viz., MCM-41, to form V—Al-MCM-41, and nickel impregnated onto the walls of the mesoporous support. Nickel loading is preferably in the range of 5 to 15% by weight of the catalyst. A process for the production of propylene from propane includes steps of placing the catalyst in a fixed bed reactor, introducing a flow of feedstock in a propane:oxygen:nitrogen ratio of about 6:6:88 by volume, maintaining the reactor at atmospheric pressure and in a temperature range of about 400 to 550° C., collecting the product, and separating propylene from the product. The process achieves propane conversion between about 6 to 22%, and a selectivity for propylene between about 22 and 70%, depending upon percent nickel content and temperature of the reaction.

6 Claims, 2 Drawing Sheets

CATALYST FOR OXIDATIVE DEHYDROGENATION OF PROPANE TO PROPYLENE

BACKGROUND OF THE INVENTION

1. Field of the Invention

The present invention relates to catalysts for converting alkanes to alkenes, and particularly to a catalyst for the oxidative dehydrogenation of propane to propylene.

2. Description of the Related Art

Propylene is a commercially valuable product. The reactivity of the allylic carbon makes propylene useful for the production of polypropylene, acrylonitrile, propylene oxide, propylene glycol, cumene, and other products, which are useful as final products and as intermediates in the synthesis or production of other commodities.

The majority of propylene is produced by steam hydrocracking of crude petroleum, or by distillation. However, such processes are not highly selective or produce propylene in low yield. Recently, there has been renewed interest in oxidative dehydrogenation of propane for the production of propylene. Oxidative dehydrogenation is attractive because it can be accomplished at lower temperatures than cracking or distillation processes, thereby avoiding complications and expense resulting from coking of the catalyst. Nevertheless, oxidative dehydrogenation is not currently used for the production of propylene, largely due to low yields and lack of selectivity of the currently known catalysts.

Thus, a catalyst for oxidative dehydrogenation of propane to propylene solving the aforementioned problems is desired.

SUMMARY OF THE INVENTION

The catalyst for oxidative dehydrogenation of propane to propylene includes vanadium and aluminum incorporated into the framework of a mesoporous support, viz., MCM-41, to form V—Al-MCM-41, and nickel impregnated onto the walls of the mesoporous support. Nickel loading is preferably in the range of 5 to 15% by weight of the catalyst. A process for the production of propylene from propane includes steps of placing the catalyst in a fixed bed reactor, introducing a flow of feedstock in a propane:oxygen:nitrogen ratio of about 6:6:88 by volume, maintaining the reactor at atmospheric pressure and in a temperature range of about 400 to 550° C., collecting the product, and separating propylene from the product. The process achieves propane conversion between about 6 to 22%, and a selectivity for propylene between about 22 and 70%, depending upon percent nickel content and temperature of the reaction.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
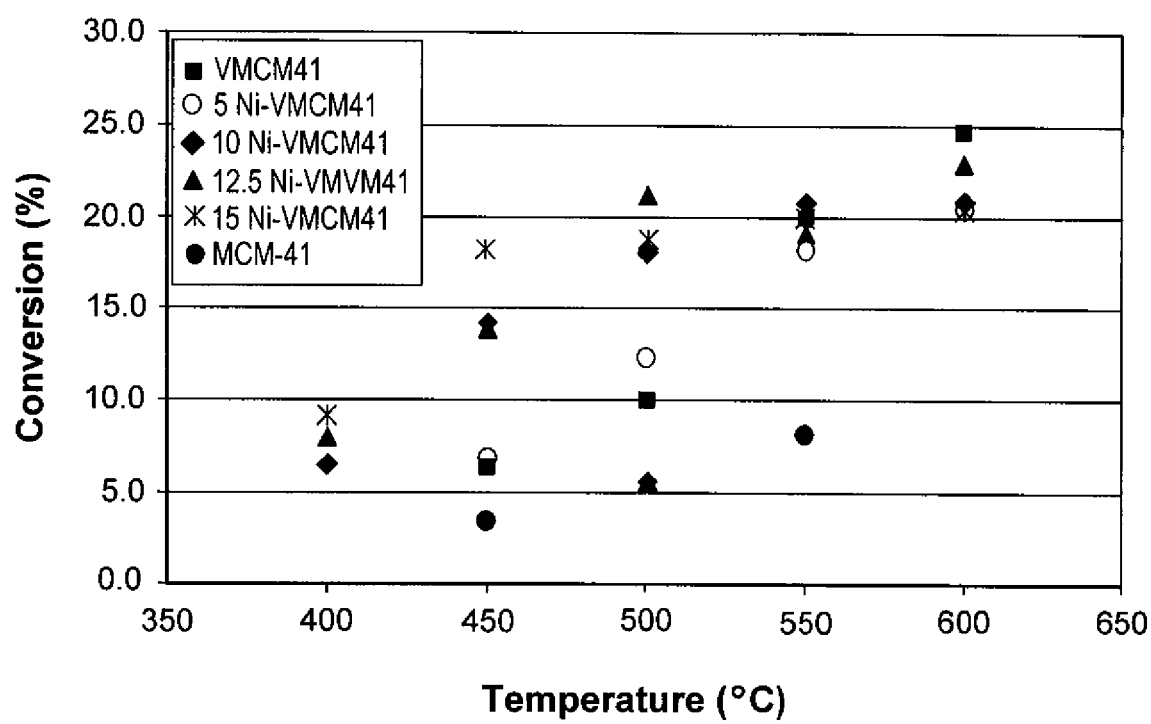
FIG. 1 is a graph showing the percent conversion of propane to propylene as a function of temperature for various samples of a catalyst for oxidative dehydrogenation of propane to propylene according to the present invention.
Figure 2:
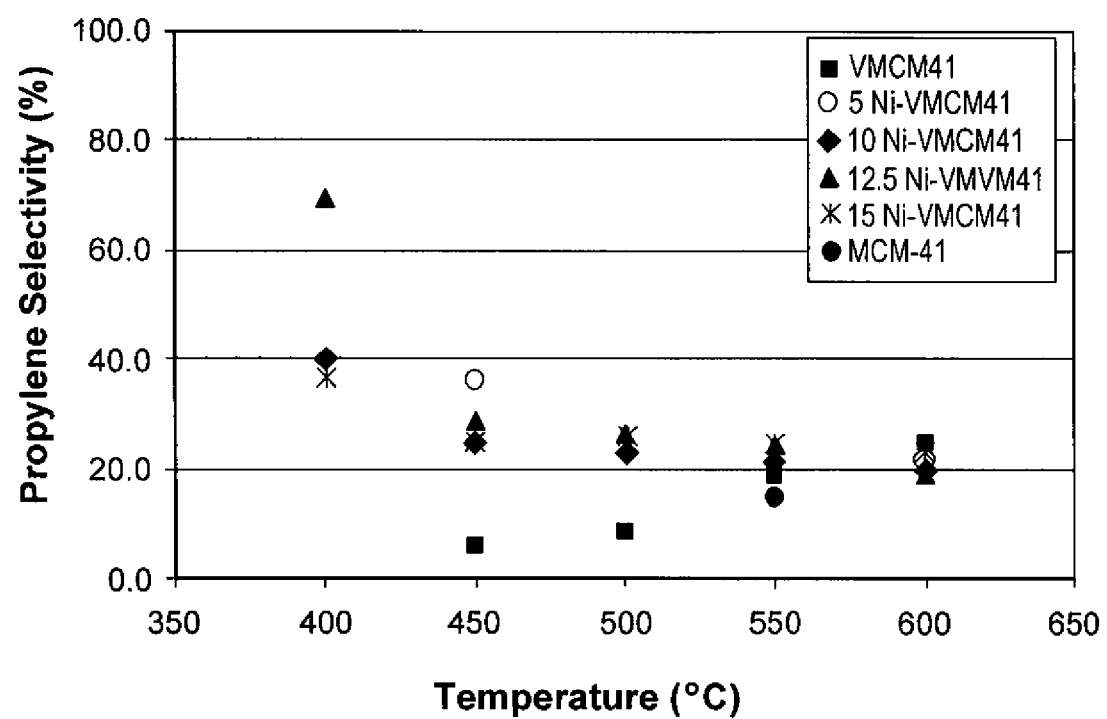
FIG. 2 is a graph showing propylene selectivity as a function of temperature for various samples of a catalyst for oxidative dehydrogenation of propane to propylene according to the present invention.

The catalyst for oxidative dehydrogenation of propane to propylene includes vanadium and aluminum incorporated into the framework of a mesoporous support, viz., MCM-41, to form V—Al-MCM-41, and nickel impregnated onto the mesoporous support. Nickel loading is preferably in the range of 5 to 15% by weight of the catalyst. A process for the production of propylene from propane includes steps of placing the catalyst in a fixed bed reactor, introducing a flow of feedstock in a propane:oxygen:nitrogen ratio of about 6:6:88 by volume, maintaining the reactor at atmospheric pressure and in a temperature range of about 400 to 550° C., collecting the product, and separating propylene from the product. The process achieves propane conversion between about 6 to 22%, and a selectivity for propylene between about 22 and 70%, depending upon percent nickel content and temperature of the reaction.

Example 1

A homogenous gel was prepared by adding appropriate amounts of ammonium metavanadate, cetyl trimethyl ammonium bromide (CTABr), sodium aluminate, and silica sol. After preparation, the homogeneous gel was transferred into a Teflon-lined autoclave reactor, which was then heated up to 97° C. for four days. During these four days, the pH was maintained at 10.5 with the addition of a solution of 30% acetic acid. Upon the reaction being completed, the reactor was cooled down, and the mixture was separated by filtration with extensive washing with deionized water in order to remove any unwanted species, such as sodium, chloride, and nitrate ions, etc. After filtration, the solid sample was dried in air in the oven at a temperature of 100° C. overnight. The template was removed by calcining the sample in a muffle furnace at a temperature of 550° C. with a heating rate of 2° C./min, starting from room temperature. The sample was kept at this temperature for 6 hours and then cooled to room temperature.

The vanadium incorporated MCM-41 (V-MCM-41) was impregnated with a desired solution of nickel nitrate via wetness incipient impregnation method. The nickel-impregnated V-MCM-41 was dried in air in the oven at a temperature of 100° C. overnight. The nitrate was removed by calcining the sample in a muffle furnace at heating rate of 5° C./min from room temperature to 500° C. for one hour, and then cooled to room temperature.

The Ni loading was tested in the range of 5 to 15% by weight of the catalyst, and more particularly, at 5% (sample 4), 10% (sample 5), 12.5% (sample 6), and 15% (sample 7), respectively.

Example 2

The catalytic properties of the Ni-supported vanadium-aluminum-containing MCM-41 catalysts were evaluated for oxidative dehydrogenation of propane in a fixed bed microreactor. The feed composition was maintained at ratio of propane:oxygen:nitrogen equal to 6:6:88 cc/min at atmospheric pressure over a temperature range of 400 to 550° C.

These samples were compared to a sample of MCM-41 without metal loading (sample 1); a sample of MCM-41 loaded with vanadium, but without nickel (sample 2); and a sample of MCM-41 impregnated with nickel, but without vanadium (sample 3). The results are reported in Table 1.

TABLE 1

Results of OXDH of propane over Ni/V-MCM-41 catalysts

| Sample No. | Catalyst/ Temp. (° C.) | Propane Conversion (%) | Selectivity (%) | | | | |
|---|---|---|---|---|---|---|---|
| | | | Ethylene | Propylene | CO | $CO_2$ | $H_2$ |
| 1 | MCM41 | | | | | | |
| | 450 | 3.30 | 0.00 | 27.78 | 0.00 | 72.22 | 0.00 |
| | 500 | 5.31 | 0.00 | 25.74 | 34.48 | 39.78 | 0.00 |
| | 550 | 8.12 | 2.42 | 14.70 | 33.98 | 48.90 | 0.00 |
| 2 | VMCM41 | | | | | | |
| | 450 | 6.23 | 0.00 | 5.41 | 0.00 | 92.81 | 1.78 |
| | 500 | 9.88 | 0.93 | 8.54 | 26.62 | 59.76 | 4.16 |
| | 550 | 19.93 | 1.89 | 18.85 | 43.58 | 31.36 | 4.32 |
| 3 | NiMCM41 | | | | | | |
| | 450 | 0.61 | 0.00 | 32.77 | 0.00 | 67.23 | 0.00 |
| | 500 | 5.76 | 0.00 | 23.42 | 0.00 | 76.58 | 0.00 |
| | 550 | 99.6 | 0.00* | 0.00 | 11.53 | 4.16 | 63.0 |
| 4 | 5% Ni/VCM41 | | | | | | |
| | 450 | 6.72 | 0.00 | 35.84 | 24.94 | 39.23 | 0.00 |
| | 500 | 12.35 | 0.00 | 23.26 | 33.70 | 43.04 | 0.00 |
| | 550 | 18.11 | 1.01 | 22.05 | 37.20 | 37.91 | 1.83 |
| 5 | 10% Ni/VMCM41 | | | | | | |
| | 400 | 6.41 | 0.00 | 40.12 | 0.00 | 59.88 | 0.00 |
| | 450 | 14.05 | 0.00 | 24.69 | 20.96 | 54.35 | 0.00 |
| | 500 | 18.06 | 0.00 | 22.98 | 22.82 | 50.76 | 3.43 |
| | 550 | 20.71 | 0.88 | 23.29 | 28.66 | 39.69 | 7.48 |
| 6 | 12.5% Ni/VMCM41 | | | | | | |
| | 400 | 8.06 | 0.00 | 69.68 | 0.00 | 30.32 | 0.00 |
| | 450 | 13.84 | 0.00 | 28.61 | 23.41 | 47.98 | 0.00 |
| | 500 | 21.20 | 0.00 | 23.445 | 27.25 | 47.08 | 2.22 |
| | 550 | 19.28 | 0.88 | 22.23 | 32.30 | 42.79 | 1.81 |
| 7 | 15% Ni/VMCM41 | | | | | | |
| | 400 | 9.11 | 0.00 | 36.44 | 10.69 | 52.86 | 0.00 |
| | 450 | 18.21 | 0.00 | 24.87 | 19.84 | 55.30 | 0.00 |
| | 500 | 18.69 | 0.00 | 26.00 | 20.79 | 50.17 | 3.04 |
| | 550 | 19.93 | 0.72 | 24.33 | 26.09 | 42.22 | 6.65 |

*$CH_4$ = 21.26

A maximum selectivity of 69.68% (with a propane conversion rate of 8.06%) was achieved for propylene using 12.5 wt. % Ni on V—Al-MCM-41 catalyst at 400° C. (sample 6). On the other hand, 5.41% selectivity for propylene was observed with V-MCM-41 (without nickel) at 450° C. (with a propane conversion rate of 6.23%; sample 2). In a comparative example of MCM-41 catalyst (without any transition metals supported), the selectivity of propylene was 27.78% at a propane conversion of 3.3% at 450° C. (sample 1). This clearly demonstrates high selectivity of propylene for the catalyst composition of nickel supported V—Al-MCM-41. The Ni-based composition resulted in low $CO_2$ selectivity as compared to V-MCM-41 and MCM-41 catalysts.

A small amount of $H_2$ besides $CO_x$ was produced during catalytic runs under the conditions of catalyst performance evaluation described above.

It will be seen that the catalyst for oxidative dehydrogenation of propane to propylene provides an alternative route for converting propane to propylene that has low energy consumption compared to conventional steam cracking, distillation, and other processes. Moreover, the catalyst is expected to have longer life due to the milder reaction conditions that avoid coking and the associated downtime required to regenerate the catalyst.

It is to be understood that the present invention is not limited to the embodiments described above, but encompasses any and all embodiments within the scope of the following claims.

We claim:

1. A catalyst for oxidative dehydrogenation of propane to propylene, comprising:
    MCM-41 forming a mesoporous support having vanadium and aluminum or oxides thereof incorporated into a framework thereof; and
    nickel or salts thereof impregnated into walls of the mesoporous support.

2. The catalyst for oxidative dehydrogenation of propane to propylene according to claim 1, wherein the nickel forms between 5% and 15% by weight of the catalyst.

3. The catalyst for oxidative dehydrogenation of propane to propylene according to claim 1, wherein the nickel forms about 12.5% by weight of the catalyst.

4. A catalyst for oxidative dehydrogenation of propane to propylene, consisting essentially of:
    MCM-41 forming a mesoporous support having vanadium and aluminum or oxides thereof incorporated into a framework thereof; and
    nickel or salts thereof impregnated into walls of the mesoporous support.

5. The catalyst for oxidative dehydrogenation of propane to propylene according to claim 4, wherein the nickel forms between 5% and 15% by weight of the catalyst.

6. The catalyst for oxidative dehydrogenation of propane to propylene according to claim 4, wherein the nickel forms about 12.5% by weight of the catalyst.

* * * * *